United States Patent [19]

Kenney et al.

[11] Patent Number: 5,166,197
[45] Date of Patent: Nov. 24, 1992

[54] PHTHALOCYANINE PHOTOSENSITIZERS FOR PHOTODYNAMIC THERAPY

[76] Inventors: Malcolm E. Kenney, 1203 Hereford Rd., Cleveland Hts.; Nancy L. Oleinick, 3727 Meadowbrook Blvd., University Hts., both of Ohio 44118; Boris D. Rihter, 2130 Murray Hill Rd., Cleveland, Ohio 44106

[21] Appl. No.: 554,290

[22] Filed: Jul. 17, 1990

[51] Int. Cl.$^5$ .................. C09B 47/04; C09B 47/08; C07F 7/18; A61K 31/40
[52] U.S. Cl. .................... 514/63; 514/183; 540/128; 556/413
[58] Field of Search ................ 540/128; 514/183, 63

[56] References Cited

U.S. PATENT DOCUMENTS 3,094,536  6/1963  Kenney et al. ............... 540/128

OTHER PUBLICATIONS

"A New Class of Mammalian Cell Photosensitizers with a Potential for Cancer Phototherapy", *Int. J. Radiat. Biol.* 47, 145–147, 1985, Ben-Hur et al.
"Activity of Phthalocyanine Photosensitizers against Human Glioblastoma in vitro", *Neurosurgery*, vol. 21, No. 4, pp. 468–473, 1987; Abernathy et al.
"Tissue Uptake, Distribution, and Potency of the Photoactivatable Dye Chloroaluminum Sulfonated . . . ", *Cancer Res.*, 48, pp. 3040–3044, 1988; Chan et al.
"The Role of Singlet Oxygen in the Photohemolysis of Red Blood Cells Sensitizied . . . ", *Photochem. Photobiol.* 46, pp. 625–632, 1987; Sonoda et al.
"Evaluation of Sulofnated Aluminum Phthalocyanines for Use in Photochemotherapy", *Cancer Letters*, 44, pp. 7–15, 1989, Bommer et al.
"The Effect of Substituents on Phthalocyanine Phototoxicity", *Photochem. Photobiol.* 46, pp. 959–963, 1987, Rosenthal et al.
"Synthesis and Photocytoxicity of Some New Substituted Phthalocyanines" *Photochem. Photobiol.* 49, pp. 279–284, 1989; Leznoff et al.
Kane et al., Inorgamic Chemistry, vol. 90, 1970, pp. 1445–1448.
*The Merck Manual*, 15th Ed., 1987, Robert Berkow Ed., pp. 1219–1220, 1227.

*Primary Examiner*—Mukund J. Shah
*Assistant Examiner*—Philip I. Datlow
*Attorney, Agent, or Firm*—Fay, Sharpe, Beall, Fagan, Minnich & McKee

[57] ABSTRACT

The present invention relates to a series of novel phthalocyanine compositions (or compounds) suitable for use as photosensitizers for photodynamic therapy. Specifically, the invention relates to a series of new aluminum (Al) and/or silicon (Si) phthalocyanines having substituted amine or quaternary ammonium axial ligands attached to the central metal, and the use of these new phthalocyanine compositions for the treatment of cancer through photosensitization. Moreover, the present invention is directed to the methods of preparing these compositions for use in photodynamic therapy.

7 Claims, 2 Drawing Sheets

PHTHALOCYANINE PHOTOSENSITIZERS FOR PHOTODYNAMIC THERAPY

BACKGROUND OF THE INVENTION

The present invention is directed to a series of novel phthalocyanines suitable for use as photosensitizers for photodynamic therapy. More particularly, the present invention is directed to a series of new aluminum (Al) and silicon (Si) phthalocyanines having substituted amine or quaternary ammonium axial ligands, and the use of these new phthalocyanine compositions for the therapeutic treatment of cancer. In addition, the present invention is directed to the methods of synthesizing these new compositions.

Photodynamic therapy, PDT, is a relatively new process for treating cancer wherein visible light is used to activate a substance, such as a dye or drug, which then attacks, through one or more photochemical reactions, the tumor tissue thereby producing a cell killing, or cytotoxic, effect. It has been discovered that when certain non-toxic photodynamic sensitizers, such as hematoporphyrin derivative ("HpD" or "Photofrin I"), which is extracted from serum and/or components thereof, are applied intravenously, topically, intradermally, etc., to the human or animal body, they are selectively retained by the cancerous tissue while being eliminated by the healthy tissue. As a result, after the administration of a photodynamic substance and the waiting of a certain period of time depending upon the type of photosensitizer utilized (i.e. two to three days after HpD treatment), substantially higher levels of the photosensitizer are retained in the cancerous tissue.

The tumor or cancerous tissue containing the photosensitizer can then be exposed to therapeutic light of an appropriate wavelength and at a specific intensity for activation. The light can be directly applied through the skin to the cancerous area from a conventional light source (e.g. laser, sun lamp, white light sources with appropriate filters, etc.), or in cases where the cancerous tissue is located deeper within the body, through surgical or non-surgical entry such as by the use of fiber optic illumination systems, including flexible fiber optic catheters, endoscopic devices, etc. The light energy and the photosensitizer cause a photochemical reaction which kills the cell in which the photosensitizer resides.

As a result, by applying a photosensitizer to the animal or human body, waiting for a sufficient period of time for the photosensitizer to permeate throughout the body while dissipating from normal tissue more rapidly than from cancer tissue, and exposing the cancerous region during the sensitive period to suitable light of sufficient intensity, the preferential destruction of the cancerous tissue will occur.

The mechanisms by which the photosensitizers produce their killing effect on the host cells upon illumination by an appropriate light source are not precisely defined and are the subject of continuing research. However, it is thought that there are at least two general mechanisms by which the photosensitizers are chemically altered upon illumination. The first general reaction mechanism involves energy transfer from the excited photosensitizer to oxygen present in the cancerous tissue. The excited photosensitizer transfers its additional energy to the oxygen, producing singlet molecular oxygen (SMO or $^1O_2$) which consequentially alters essential cell components.

More particularly, in the first general reaction mechanism, it is thought that the light energy causes the photosensitizer to become excited from the ground state, $S_0$, to the first excited singlet state, $S_1$. The photosensitizer's excited singlet state, $S_1$, is then transformed by intramolecular coupling to the lowest lying triplet state $T_1$. Through a direct intermolecular process discussed more particularly by John G. Parker of The John Hopkins University, Baltimore, Md., in U.S. Pat. Nos. 4,576,173; 4,592,361; and 4,827,938, the photosensitizer transfers this energy to oxygen molecules present in the tissue and raises them from the ground triplet to the first excited electronic singlet state, $^1O_2$. The singlet molecular oxygen, $^1O_2$, destroys or alters vital cellular components such as the cell membrane, etc., ultimately inducing necrosis and destroying the cancerous tissue.

The process by which biological damage occurs as a result of the optical excitation of a photosensitizer in the presence of oxygen is generally referred to as "photodynamic action". A more detailed discussion concerning the use of photodynamic action in the treatment of cancer is discussed by Thomas J. Dougherty, William R. Potter, and Kenneth R. Weishaupt of Health Research, Inc., Buffalo, N.Y., in a series of patents, i.e. U.S. Pat. Nos. 4,649,151; 4,866,168; 4,889,129; and 4,932,934, concerning improved hematoporphyrin and porphyrin derivatives including dihematoporphyrin ether (DHE), the purified form of HpD, and methods utilizing same, for photodynamic therapy.

The second general mechanism thought to be involved in the killing effect produced by certain photosensitizers involves the production of free radicals. Subsequent reactions of the radicals with organic molecules and/or with oxygen results in the biochemical destruction of the diseased tissue.

Although the exact effective mechanisms of the photochemical reactions which produce death of the cancer cells is not clearly understood and varies depending upon the type of photosensitizer utilized, what is clear is that photodynamic therapy is effective for the preferential destruction of cancerous tissue. Furthermore, photodynamic therapy has several attractive features over conventional methods for treating cancer such as chemotherapy, radiation, surgical procedures, etc., in that the photosensitizers utilized are generally non-toxic, concentrate or remain preferentially in cancer cells, can be utilized with other modes of treatment since PDT does not interfere with other chemicals or processes, etc.

As a result, photodynamic therapy is now used experimentally for the treatment of malignant diseases in humans and animals. For example, photodynamic therapy has been used successfully for the treatment of a broad range of cancers including metastatic breast tumors, endometrial carcinomas, bladder tumors, malignant melanoma, Kaposi's sarcoma, basal cell carcinoma, chondrosarcoma, squamous cell carcinoma, prostate carcinoma, laryngeal papillomas, mycosis fungoides, superficial cancer of the tracheobronchial tree, cutaneous/mucosal papilloma, gastric cancer, enteric cancer, etc.

The drug in current clinical use is "Photofrin II", a purified version of hematoporphyrin derivative (HpD, or "Photofrin I"). HpD and Photofrin II are complex mixtures of substances and have been the subject of numerous investigations to identify their active compounds. In addition, other porphyrins and porphyrin-like compounds such as chlorins (see U.S. Pat. Nos.

4,656,186; 4,693,885; and 4,861,876) and enlarged porphyrins, naphthalocyanines, phthalocyanines, platyrins, porphycenes (see U.S. Pat. Nos. 4,649,151 and 4,913,907), purpurins, texaphyrins, and verdins have been investigated as photosensitizers. Numerous other substances, such as "merocyanine 540", xanthenes (Rhodamine 123 6 G&B) cationic cyanic dyes, chalcogenapyrylium dyes, phenothiazinium derivatives, tetracycline, berbine sulphate, acridine orange, and fluorescein have also been used as photosensitizers, however, the porphyrin derivatives are generally preferred because they absorb in the long wave length region (red region) of the visible spectrum.

The specific reactions used by many of the above substances to produce the killing effect in cancer cells on exposure to excitory light are in most instances not known or well understood. As mentioned above, research continues in this area in order to more fully understand the cytotoxic effects produced by the various photosensitizers.

Notwithstanding the above, although many of the above identified substances have demonstrated enhanced effects in photodynamic therapy, these substances also produce various side effects which limit their use for photodynamic therapy. The most predominant side effect exhibited by many of the currently utilized substances is the development of uncontrolled photosensitivity reactions in patients after the systemic administration of the photosensitizer and the exposure of the patient to normal sunlight. In this regard, on exposure to the sun, the photodynamic therapy patients can develop generalized skin photosensitization. As a result, the patient after receiving systemic injections of a photosensitizing substance is required to avoid bright light, especially sunlight for periods of about four to eight weeks.

Furthermore, since many of the above photosensitizers bind to other non-cancerous cells, some healthy cell destruction can also occur. Similarly, although many of the photosensitizers are soluble in water, large dosages are required for cellular uptake and/or treatment. Thus, use of many of the above indicated photosensitizers is normally limited to patients with severe cancerous tumors and continuing research is being conducted in order to produce photosensitizing substances, and/or methods of administering such substances, that avoid these side reactions as well as produce enhanced photosensitizing effects.

Considerable attention has recently been directed to a group of compounds having the phthalocyanine ring system. These compounds, called phthalocyanines, are a group of photoactive dyes that are somewhat structurally similar (i.e. have nitrogen containing ring structure) to the porphyrin family. Phthalocyanines are azaporphyrins consisting of four benzoindole nuclei connected by nitrogen bridges in a 16-membered ring of alternating carbon and nitrogen atoms around a central metal atom (i.e. $C_{32}H_{16}N_8M$) which form stable chelates with metal cations. In these compounds, the ring center is occupied by a metal ion (such as a diamagnetic or a paramagnetic ion) that may, depending on the ion, carry one or two simple ligands. In addition, the ring periphery may be either unsubstituted or substituted.

Since E. Ben-Hur and I. Rosenthal disclosed the potential use of phthalocyanines as photosensitizers in 1985 (E. Ben-Hur and I. Rosenthal, The phthalocyanines: A new class of mammalian cell photosensitizers with a potential for cancer photherapy, *Int. J. Radiat. Biol.* 47, 145–147, 1985), a great deal of research has followed producing a number of phthalocyanines for photodynamic therapy. Although prior studies with phthalocyanines have been generally disappointing, primarily because of the poor solubility characteristics of the basic ring, some of these compounds have attractive characteristics.

For example, unlike some of the porphyrin compounds, phthalocyanines strongly absorb clinically useful red light with absorption peaks falling between about 600 and 810 nm (Abernathy, Chad D., Anderson, Robert E., Kooistra, Kimberly L., and Laws, Edward R., Activity of Phthalocyanine Photosensitizers against Human Glioblastoma in Vitro, *Neurosurgery*, Vol. 21, No. 4, pp. 468–473, 1987). Although porphyrins absorb light poorly in this wavelength region, as a result of the increased transparency of biological tissues at longer wavelengths, red light is normally used for photodynamic therapy. Thus, the greater absorption of red light by the phthalocyanines over porphyrins indicates deeper potential penetration with the phthalocyanines in photodynamic treatment processes.

Furthermore, it has been found that the addition of certain metal cations (i.e. diamagnetic metal cations such as aluminum) to the phthalocyanine ring will, in some instances, create a fairly stable chelate with enhanced photosensitizing tumoricidal activity. While the mechanisms for producing the photoreactions are not clear (i.e. it is not known whether singlet oxygen or hydroxyl radicals, etc. are produced), the choice of the metal cation is apparently critical in that certain metals (i.e., paramagnetic metals) may actually inhibit the phototoxic properties of the resulting compound. Abernathy, et al., pp. 470–471.

In addition, the phthalocyanines offer many benefits over the porphyrin components as photosensitizers in that the phthalocyanines are relatively easy to synthesize, purify, and characterize in contrast to the porphyrins, which are often difficult to prepare. Similarly, the metal phthalocyanines are exceptionally stable compounds in comparison to the porphyrin or porphyrin-like compounds. As a result, certain metallic phthalocyanines, such as aluminum phthalocyanine tetrasulfonate (AlPcS) and chloroaluminum phthalocyanine (AlPcCl), offer a number of advantages over porphyrins as therapeutic agents for photodynamic therapy.

However, notwithstanding some of the benefits indicated above, only a few of the many possible types of ring-substituted phthalocyanines belonging to this group have been examined. By far the most attention has been given to sulfonated phthalocyanines and to phthalocyanines with peripheral substituents carrying hydroxy, alkoxy, and amino substituents. Very little attention has been given to phthalocyanines with complex metal ligands.

The limited variety of phthalocyanines which have been tested vary greatly in their photosensitizing activity. Metal-free phthalocyanines show poor photodynamic activity (Abernathy, C. D., R. E. Anderson, K. L. Kooistra, & E. R. Laws, Jr., "Activity of Phthalocyanine Photosensitizers Against Human Glioblastoma in vitro", *Neurosurgery* 21, pp. 468–473, 1987; Chan, W. S., J. F. Marshall, G. Y. F. Lam, & I. R. Hart, "Tissue Uptake, Distribution, and Potency of the Photoactivatable Dye Chloroaluminum Sulfonated Phthalocyanine in Mice Bearing Transplantable Tumors", *Cancer Res.* 48, pp. 3040–3044, 1988; Sonoda, M., C. M. Krishna, & P. Riesz, "The Role of Singlet Oxygen in the Photohemolysis of Red Blood Cells Sensitized by Phthalocyanine Sulfonates", *Photochem. Photobiol.* 46, pp. 625-632, 1987) as do phthalocyanines containing paramagnetic metals. In contrast, those containing diamagnetic metals, such as Al, Sn, and Zn, are active as a result of the long half-life of the triplet state (Chan, W. S., J. F. Marshall, G. Y. F. Lam, & I. R. Hart, "Tissue Uptake, Distribution, and Potency of the Photoactivatable Dye Chloroaluminum Sulfonated Phthalocyanine in Mice Bearing Transplantable Tumors", *Cancer Res.* 48, pp. 3040-3044, 1988; Sonoda, M., C. M. Krishna, & P. Riesz, "The Role of Singlet Oxygen in the Photohemolysis of Red Blood Cells Sensitized by Phthalocyanine Sulfonates", *Photochem. Photobiol.* 46, pp. 625-632, 1987). While in general there appears to be an increase in photosensitizing ability with lipophilicity (Berg, K., J. C. Bommer, & J. Moan, "Evaluation of Sulfonated Aluminum Phthalocyanines for use in Photochemotherapy. Cellular Uptake Studies", *Cancer Letters* 44 pp. 7-15, 1989) some highly lipophilic derivatives, such as a tetraneopentoxy derivative, are poor photosensitizers (Rosenthal, I., E. Ben-Hur, S. Greenberg, A. Concepcion-Lam, D. M. Drew, & C. C. Leznoff, "The Effect of Substituents on Phthalocyanine Phototoxicity", *Photochem. Photobiol.* 46, pp. 959-963, 1987).

Recently, Leznoff, et al. (Leznoff, C. C., Vigh, S., Svirskaya, P. I., Greenberg, S., Drew, D. M., Ben-Hur, E. & Rosenthal, I., "Synthesis and Photocytoxicity of Some New Substituted Phthalocyanines", *Photochem. Photobiol.* 49, pp. 279-284, 1989) synthesized a series of ring-substituted phthalocyanines. The substituents were hydroxy or alkoxy groups, as well as substituted amines. Of this series, a Zn phthalocyanine with four diethylaminopropyl groups was reported to have some photosensitizing activity against Chinese hamster fibroblast V79 cells in culture. However, it is critical to note that although amine groups were present in the Zn phthalocyanine compound containing the four diethylaminopropyl groups, the amine groups were ring substituents and no simple axial ligands were specified.

For some time the applicants have been searching for phthalocyanines having superior photosensitizing ability. In this search, the applicants have emphasized compounds with complex metal ligands. Initially, applicants examined the photocytotoxicity of twenty-one phthalocyanines taken from a collection in the applicants' laboratories to Chinese hamster fibroblasts, i.e. V79 cells. One of these phthalocyanines was HOSiPcOSi(CH$_3$)$_2$(CH$_2$)$_3$OCH$_2$CHOHCH$_2$N(C$_2$H$_5$)$_2$, a phthalocyanine composition carrying a hydroxyl amine functional group. This was found to be taken up efficiently by the Chinese hamster fibroblast V79 cells and to have excellent photocytotoxicity. However, solutions of this composition in dimethylformamide were found to decompose relatively rapidly. Further, it appeared that the composition might have dark toxicity (i.e. be toxic to tissues in the absence of light) in vivo because of its —OCHOHCH$_2$NR$_2$ functional group.

With the results of this preliminary work in mind, the applicants then prepared and studied a series of new aluminum and silicon phthalocyanines having relatively simple ligands carrying NR$_2$ or NR$_3$+ functions. The present invention is the result of applicants' studies of these compounds, and the use of the same for photodynamic therapy.

SUMMARY OF THE INVENTION

In one aspect, the present invention is directed to a series of phthalocyanine compounds (or compositions) with modifying moieties linked to the central metal, which is either aluminum (Al) or silicon (Si). Specifically, the present invention relates to a series of aluminum or silicon phthalocyanines having an axial group, or groups, carrying, or terminating in, an amine or quaternary ammonium function. The specific embodiments of the invention can be generally characterized by the following Formula I:

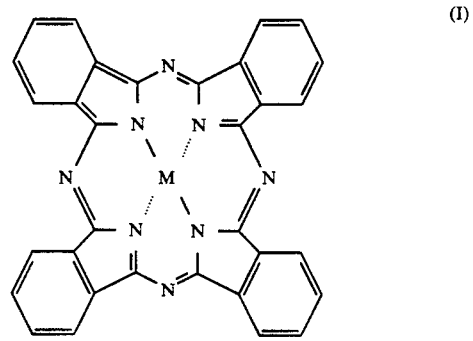

wherein:
M=AlOsi(CH$_3$)$_2$(CH$_2$)$_3$N(CH$_3$)$_2$;
AlOsi(CH$_3$)$_2$(CH$_2$)$_3$N(CH$_3$)$_3$+I−;
CH$_3$SiOSi(CH$_3$)$_2$(CH$_2$)$_3$N(CH$_3$)$_2$;
HOSiOSi(CH$_3$)$_2$(CH$_2$)$_3$N(CH$_3$)$_2$;
HOSiOSi(CH$_3$)$_2$(CH$_2$)$_3$N(CH$_3$)$_3$+I−; or
Si[OSi(CH$_3$)$_2$(CH$_2$)$_3$N(CH$_3$)$_3$+I−]$_2$.

In an additional aspect, the present invention relates to the various methods of synthesizing the novel phthalocyanine compositions. The novel phthalocyanines produced by the invention exhibit enhanced characteristics which make them well suited for photodynamic therapy when utilized alone or in combination with a pharmaceutical carrier.

In a further aspect, the present invention is directed to various methods for destroying cancer tissue comprising the steps of administering to the cancer tissue an effective amount of a phthalocyanine composition having an axial group, or groups, carrying, or terminating in an amine or quaternary ammonium function, and applying light of sufficient wavelength and intensity to activate the composition thereby exerting a cell killing, or cytotoxic, effect on the cancer tissue.

BRIEF DESCRIPTION OF THE DRAWINGS

The following is a brief description of the drawings which are presented for the purpose of illustrating the invention and not for the purpose of limiting same.

DETAILED DESCRIPTION OF THE INVENTION

Figure 1:
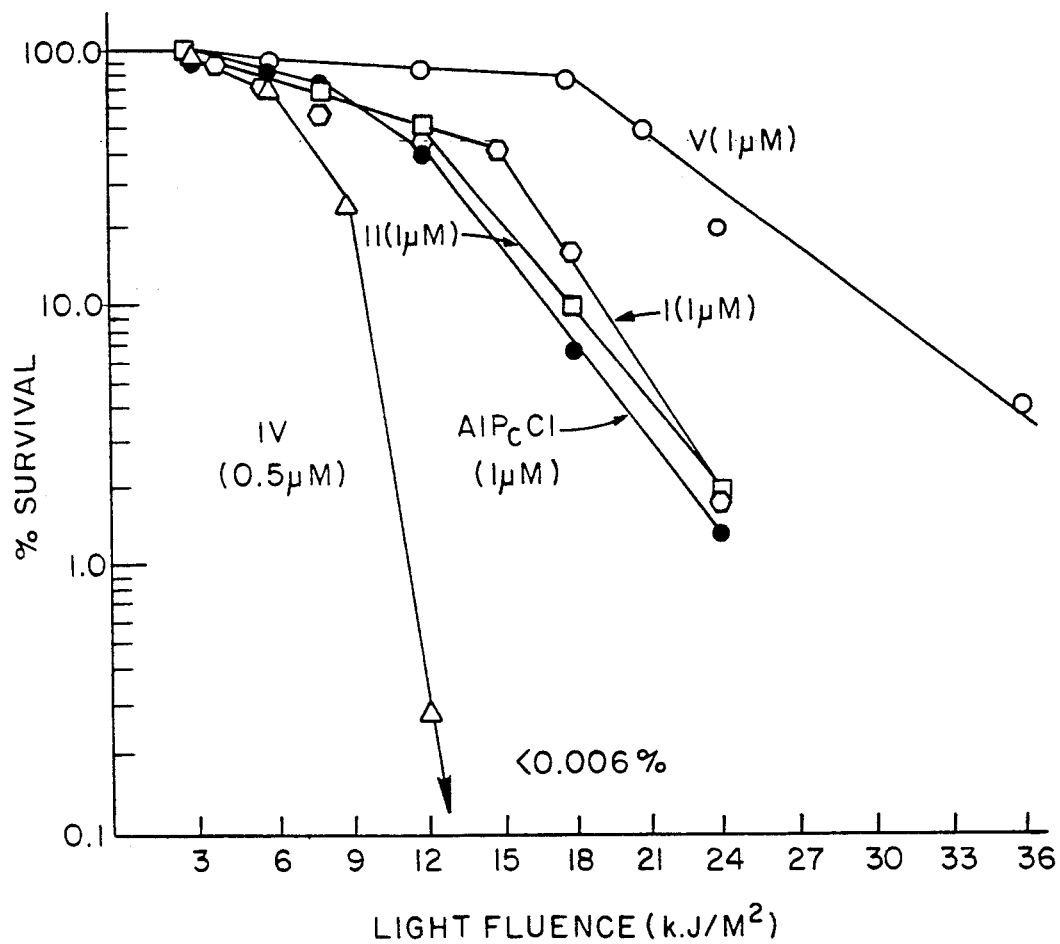
FIG. 1 is a graph illustrating the photodynamic efficacy of the various compositions of the present invention in comparison to AlPcCl. The phthalocyanine composition compounds of the present invention were tested for their photodynamic efficiency against Chinese hamster fibroblast V79 cells by colony formation. Monolayer cultures were treated with the indicated phthalocyanine composition for 18 hours, irradiated with various fluences of red light, and immediately trypsinized and replated at appropriate aliquots in triplicate. Colonies of at least 50 cells were counted after 7-10 days. The plating efficiency of the untreated cells was approximately 90%.

The present invention relates to a series of novel phthalocyanine compositions (or compounds) suitable for use as photosensitizers for photodynamic therapy. Specifically, the invention relates to a series of new aluminum (Al) and/or silicon (Si) phthalocyanines having substituted amine or quaternary ammonium axial ligands attached to the central metal, and the use of these new phthalocyanine compositions for the treatment of cancer through photosensitization. Moreover, the present invention is directed to the methods of preparing these compositions for use in photodynamic therapy.

Although research has recently been directed to the use of various phthalocyanines for photodynamic therapy, this activity has been principally directed to phthalocyanines with peripheral substituents, and little, if any, attention has been given to phthalocyanines with complex metal ligands. Along this line, in the phthalocyanine compositions described in the prior art, only simple ligands, such as Cl or OH ligands, are attached to the central metal. However, in the new compositions of the present invention, axial ligands carrying or, terminating in an amine function or a quaternary ammonium function are attached to the central metal. As a result, it is believed by the applicants that these more complex axial ligands give the new phthalocyanine compositions the potential to bind to the various species that assist in transporting the composition to and from their targets, as well as enhance the potential for the phthalocyanines to bind to their specific target cells.

This is demonstrated in that some of the novel phthalocyanines of the present invention having substituted amine or quaternary ammonium axial ligands attached to either aluminum or silicon as the central metal, are much more effective in producing photodynamic activity when compared with chloroaluminum phthalocyanine (AlPcCl). The enhanced cytotoxic effects produced are due to the increased cellular uptake of the compositions and/or the increased loss of clonogenicity as a function both of the concentration of the phthalocyanine and the red light fluence.

More particularly, in applicants' investigation for phthalocyanines exhibiting enhanced photosensitizing ability through the synthesis and evaluation of a number of phthalocyanine compositions having complex metal ligands, the applicants have produced a series of new aluminum and silicon phthalocyanines having substituted amine or quaternary ammonium axial ligands. In this regard, two silicon phthalocyanines and one aluminum phthalocyanine with axial groups terminating in an amine function were prepared: SiPc(CH$_3$)(OSi(CH$_3$)$_2$(CH$_2$)$_3$N(CH$_3$)$_2$), SiPc(OH)-(OSi(CH$_3$)$_2$(CH$_2$)$_3$N(CH$_3$)$_2$, and AlPcOSi(CH$_3$)$_2$(CH$_2$)$_3$N(CH$_3$)$_2$. In addition, two silicon phthalocyanines and one aluminum phthalocyanine with axial groups terminating in a quaternary ammonium function were prepared: SiPc(OH)-(OSi(CH$_3$)$_2$(CH$_2$)$_3$N(CH$_3$)$_3$+I$^-$, SiPc-(OSi(CH$_3$)$_2$(CH$_2$)$_3$N(CH$_3$)$_3$+I$^-$)$_2$, and AlPcOSi(CH$_3$)$_2$(CH$_2$)$_3$N(CH$_3$)$_3$+I$^-$.

The new phthalocyanine compositions can be generally characterized by the following formula:

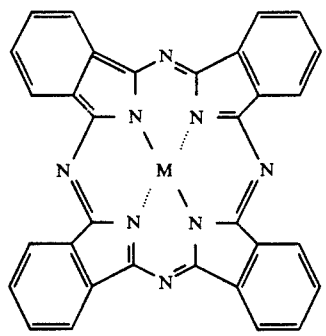

wherein:
M = AlOSi(CH$_3$)$_2$(CH$_2$)$_3$N(CH$_3$)$_2$;
AlOSi(CH$_3$)$_2$(CH$_2$)$_3$N(CH$_3$)$_3$+I$^-$;
CH$_3$SiOSi(CH$_3$)$_2$(CH$_2$)$_3$N(CH$_3$)$_2$;
HOSiOSi(CH$_3$)$_2$(CH$_2$)$_3$N(CH$_3$)$_2$;
HOSiOSi(CH$_3$)$_2$(CH$_2$)$_3$N(CH$_3$)$_3$+I$^-$; or
Si[OSi(CH$_3$)$_2$(CH$_2$)$_3$N(CH$_3$)$_3$+I$^-$]$_2$.

The new phthalocyanine compositions bearing the substituted amine or quaternary ammonium axial ligands have been evaluated for their photodynamic efficiency against Chinese hamster fibroblast V79 cells in vitro. Chloroaluminum phthalocyanine (AlPcCl) was used as a reference compound. Along this line, the compounds, SiPc(CH$_3$)OSi(CH$_3$)$_2$(CH$_2$)$_3$N(CH$_3$)$_2$ and SiPc((OSi(CH$_3$)$_2$(CH$_2$)$_3$N(CH$_3$)$_3$+I$^-$)$_2$, were found to be inactive as photosensitizers owing to poor cellular uptake. The most efficient photosensitizer, as judged by uptake, growth delay, and photocytotoxicity, was SiPc-(OH)OSi(CH$_3$)$_2$(CH$_2$)$_3$N(CH$_3$)$_2$. The related quaternary ammonium compound, SiPc(OH)OSi(CH$_3$)$_2$(CH$_2$)$_3$N(CH$_3$)$_3$+I$^-$, displayed poorer uptake but induced marked photocytotoxicity. When expressed as a function of the product of intracellular phthalocyanine and the fluence reducing cell survival to 10%, this quaternary ammonium compound was the most efficient photosensitizer.

The specific process utilized to synthesize the aluminum and silicon phthalocyanine compounds of the present invention, and the enhanced results produced through the use of these new compounds for photodynamic therapy, are more particularly described below in the following example.

EXAMPLE 1

Synthesis of Phthalocyanines

CH$_3$OSi(CH$_3$)$_2$(CH$_2$)$_3$N(CH$_3$)$_2$ - Under argon gas a solution of CH$_3$MgCl in tetrahydrofuran (3.0M, 45 mL) was added dropwise to a cool (ice bath) solution of (CH$_3$O)$_3$Si(CH$_2$)$_3$N(CH$_3$)$_2$ (11 mL) in tetrahydrofuran (100 mL), and the resulting suspension was stirred for 2 hours while being kept cool (~5° C.). Methanol (20 mL) then was added to the suspension and the mixture formed was filtered. The solid was washed with ether (50 mL) and the washings and filtrate were combined and concentrated with a rotary evaporator (45° C.). The concentrate was fractionally distilled under vacuum (45 torr) and a selected fraction (86°–88° C., 5.0 g.) was retained (55%): NMR (CDCl$_3$) $\delta$ 3.42 (s, CH$_3$O), 2.24 (m, $\gamma$-CH$_2$), 2.20 (s, NCH$_3$), 1.49 (m, $\beta$-CH$_2$), 0.57 (m, $\alpha$-CH$_2$), 0.10 (s, CH$_3$Si).

The compound is a colorless liquid.

AlPcOSi(CH$_3$)$_2$(CH$_2$)$_3$N(CH$_3$)$_2$ - Compound I

A mixture of CH$_3$OSi(CH$_3$)$_2$(CH$_2$)$_3$N(CH$_3$)$_2$ (203 mg) produced above and a suspension of AlPcOH.'x-H$_2$O (56 mg) and 2-ethylpyridine (15 mL) that had been dried by distillation (3 mL of distillate) was refluxed for 45 minutes and filtered. The filtrate was evaporated to dryness with a rotary evaporator ($\sim$40° C.) and the solid was dissolved CH$_2$Cl$_2$ (2 mL). Hexanes (3 mL) were added to the solution and the resulting suspension was filtered. The solid was washed (benzene and hexanes), vacuum dried (65° C.), and weighed (63 mg, 98% assuming AlPcOH.3H$_2$O); NMR (C$_5$D$_5$N, 70° C.) $\delta$ 9.65 (m, 1,4-PcH), 8.28 (m, 2,3PcH), 1.63 (s, NCH$_3$), 0.99 (m, $\gamma$-CH$_2$), −0.50 (m, $\beta$-CH$_2$), −1.80 (m, $\alpha$-CH$_2$), −2.33 (s, SiCH$_3$).

The compound is blue and is soluble in CH$_2$Cl$_2$ and toluene.

AlPcOSi(CH$_3$)$_2$(CH$_2$)$_3$N(CH$_3$)$_3$+I− - Compound II

A mixture of AlPcOSi(CH$_3$)$_2$(CH$_2$)$_3$N(CH$_3$)$_2$ (30 mg), benzene (10 mL), and CH$_3$I (15 $\mu$L) was refluxed for 1.5 hours, cooled, and filtered. The solid was vacuum dried (60° C.) and weighed (31 mg, 86%): NMR (C$_5$D$_5$N, 70° C.) $\delta$ 9.75 (m, 1,4-PcH), 8.34 (m, 2,3-PcH), 2.90 (s, NCH$_3$), 2.02 (m, $\gamma$-CH$_2$), −0.53 (m, $\beta$-CH$_2$), −1.87 (m, $\alpha$-CH$_2$), −2.40 (s, SiCH$_3$).

The compound is a blue solid and is soluble in CH$_2$Cl$_2$ and CH$_3$OH but is insoluble in toluene and H$_2$O.

CH$_3$SiPcOSi(CH$_3$)$_2$(CH$_2$)$_3$N(CH$_3$)$_2$ - Compound III

Procedures in this synthesis that were carried out under low light conditions (room lights off, shades drawn) are identified by the symbol 1. A mixture of CH$_3$OSi(CH$_3$)$_2$(CH$_2$)$_3$N(CH$_3$)$_2$ (224 mg) and a suspension of CH$_3$SiPcOH (117 mg) and pyridine (25 mL) that had been dried by distillation (1) was slowly distilled (1) for 3 hours (10 mL of distillate) and then filtered (1, no solid). The filtrate was evaporated to dryness with a rotary evaporator (1, 75° C.), and the solid was dissolved in CH$_2$Cl$_2$ (1, 2 mL). Hexanes (30 mL) were added to the solution (1) and the resulting suspension was filtered (1). The solid was washed (hexanes), vacuum dried (65° C.), and weighed (111 mg, 76%): mp>260° C.; NMR (CDCl$_3$) $\delta$ 9.63 (m, 1,4-PcH), 8.33 (m, 2,3-PcH), 1.74 (s, NCH$_3$), 1.01 (m, $\gamma$-CH$_2$), −1.18 (m, $\beta$-CH$_2$), −2.25 (m, $\alpha$-CH$_2$), −2.96 (s, Si(CH$_3$)$_2$), −6.35 (s, SiCH$_3$).

The compound is dark green and is soluble in CH$_2$Cl$_2$ and toluene. Solutions of it are rapidly photolyzed by white light.

HOSiPcOSi(Ch$_3$)$_2$(CH$_2$)$_3$N(CH$_3$)$_2$ - Compound IV

A mixture of CH$_3$SiPcOSi(CH$_3$)$_2$(CH$_2$)$_3$N(CH$_3$)$_2$ (35 mg), N(C$_2$H$_5$)$_3$ saturated with H$_2$O (0.2 mL), and toluene (70 mL) was irradiated with an incandescent light (300 W in 35 mm slide projector) for 15 minutes. The resulting suspension was concentrated with a rotary evaporator ($\sim$45° C.) and the concentrate ($\sim$5 mL) was diluted with hexanes (1 mL). The suspension formed was filtered and the solid was washed (hexanes), vacuum dried (65° C.), and weighed (33 mg, 96%): mp>260° C.; NMR (dimethylformamide-d$_7$, 70° C.) $\delta$ 9.68 (m, 1,4-PcH), 8.47 (m, 2,3 PcH), 1.52 (s, NCH$_3$), 0.74 (m, $\gamma$-CH$_2$), −1.11 (m, $\beta$-CH$_2$), −2.27 (m, $\alpha$-CH$_2$), −2.89 (s, SiCH$_3$). MS-HRFAB exact mass m/z calculated for C$_{39}$H$_{35}$N$_9$O$_2$Si$_2$ M+ 717.2452. Found 717.2422.

The compound is blue and is soluble in CH$_2$Cl$_2$ and toluene.

HOSiPcOSi(CH$_3$)$_2$(CH$_2$)$_3$N(CH$_3$)$_3$+I− - Compound V

A mixture of HOSiPcOSi(CH$_3$)$_2$(CH$_2$)$_3$N(CH$_3$)$_2$ (24 mg), CH$_3$I (25 $\mu$L), and benzene (10 mL) was refluxed for 1.5 hours, cooled, and filtered. The solid was washed (benzene), vacuum dried (65° C.), and weighed (23 mg, 81%): NMR (dimethylformamide-d$_7$, 70° C.) $\delta$ 9.66 (m, 1,4-PcH), 8.45 (m, 2,3-PcH), 2.87 (s, NCH$_3$), 2.06 (m, $\gamma$-CH$_2$), −0.97 (m, $\beta$-CH$_2$), 2.25 (m, $\alpha$-CH$_2$), −2.83 (s, SiCH$_3$). MS-HRFAB exact mass m/z calculated for C$_{40}$H$_{38}$N$_9$O$_2$Si$_2$ (M-I)+ 732.2687. Found 732.2668.

The compound is blue. It is soluble in CH$_2$Cl$_2$ and CH$_3$OH but is insoluble in toluene and H$_2$O.

SiPc[OSi(CH$_3$)$_2$(CH$_2$)$_3$N(CH$_3$)$_2$]$_2$

A mixture of CH$_3$OSi(CH$_3$)$_2$(CH$_2$)$_3$N(CH$_3$)$_2$ (239 mg) and a suspension of SiPc(OH)$_2$ (232 mg) and 2-ethylpyridine (30 mL) that had been dried by distillation ($\sim$2 mL of distillate) was slowly distilled for 2 hours ($\sim$5 mL of distillate). The resulting solution was filtered, the filtrate was evaporated to dryness with a rotary evaporator ($\sim$60° C.), and the solid was dissolved in CH$_2$Cl$_2$ (3.5 mL). The CH$_2$Cl$_2$ solution was diluted with hexanes ($\sim$40 mL), the suspension formed was filtered, and the solid was washed (hexanes), air dried, and weighed (263 mg, 76%); NMR (CDCl$_3$), $\delta$ 9.63 (m, 1,4-PcH), 8.34 (m, 2,3-PcH), 1.65 (s, NCH$_3$), 0.90 (m, $\gamma$-CH$_2$), −1.10 (m, $\beta$-CH$_2$), −2.26 (m, $\alpha$-CH$_2$), −2.87 (s, SiCH$_3$).

The compound is blue and is soluble in CH$_2$Cl$_2$ and toluene.

SiPc[OSi(CH$_3$)$_2$(CH$_2$)$_3$N(CH$_3$)$_3$+I−]$_2$ - Compound VI

A mixture of SiPc[OSi(CH$_3$)$_2$(CH$_2$)$_3$N(CH$_3$)$_2$]$_2$ produced above (30 mg), CH$_3$I (36 $\mu$L), and benzene (5 mL) was refluxed for 1.5 hours, cooled, and filtered. The solid was washed (benzene, hexanes), vacuum dried (60° C.), and weighed (32 mg, 79%): NMR (CD$_3$OD) $\delta$ 9.63 (m, 1,4-PcH), 8.41 (m, 2,3-pcH), 2.39 (S, NCH$_3$), 1.89, (m, $\gamma$-CH$_2$), −1.10 (m, $\beta$-CH$_2$), −2.21 (m, $\alpha$-CH$_2$), −2.90 (m, SiCH$_3$).

The compound is blue and is soluble in CH$_2$Cl$_2$ and CH$_3$OH but is insoluble in toluene. It disperses in H$_2$O but does not dissolve in it.

Cell Culture

Chinese hamster V79-379 lung fibroblasts were grown in monolayer culture in McCoy's 5A medium (Gibco Laboratories, Grand Island, N.Y.) augmented with 10% calf serum and buffered with 20 mM HEPES (pH 7.4).

Uptake of Phthalocyanines

Total uptake was determined by scraping the phthalocyanine-treated monolayer, collecting the cells on a glass-fiber filter, and extracting the phthalocyanine in ethanol, as previously described by Ramakrishnan, et al., 1989. (Ramakrishnan, N., M. E. Clay, M. F. Horng, A. R. Antunez, & H. H. Evans, "DNA Lesions and DNA Degradation in Mouse Lymphoma L5178Y Cells After Photodynamic Treatment Sensitized by Chloroaluminum Phthalocyanine", *Photochem. Photobiol.*, in press, 1989). The amount of drug was determined by absorption at 674 nm and expressed relative to the number of cells, as measured in a Coulter cell counter on an aliquot of the cell population. Controls included cells not treated with drug, medium alone, and drug-containing medium without cells. The results of the total uptake of the various compositions of the present invention in comparison to AlPcCl are set forth below in Table 1.

Drug Treatment and Light Exposure

The cells were treated with 1 $\mu$M AlPcCl (from Eastman Kodak Rochester, N.Y.) or with phthalocyanine compositions I-VI (0.5-1.0 $\mu$M final concentration in the medium) for 18 hours by adding the appropriate volume of a 1.0 mM stock solution in dimethylformamide (DMF) to the culture medium. The growth medium was replaced with 4 ml Hank's balanced salt solution (HBSS), and the cells were irradiated. The light source was a 500 W tungsten-halogen lamp located approximately 29 inches below the surface of a glass exposure tray. The visible light administered to the cells was filtered to allow passage of only that portion of the visible spectrum above 600 nm (Lee Primary red filter No. 106, Vincent Lighting, Cleveland, Ohio). The fluence rate was approximately 0.074 kJ/m$^2$/s at the level of the cell monolayer.

Growth Delay

At the time of light exposure, there were approximately $1.5 \times 10^5$ cells per 25 cm$^2$ flask. Following irradiation, the HBSS was replaced by 10 ml of fresh complete growth medium, and the cultures were returned to the 37° C. incubator. At various times before and after irradiation, duplicate cultures were trypsinized and counted. Controls included untreated cells and cells treated with light alone or drug alone. In addition, in each experiment, the drug to be tested was compared to a standard treatment, i.e. 1 $\mu$M AlPcCl for 18 hours followed by 12 kJ/m$^2$ light. The results of the growth delay analysis for each of the compositions I-VI in comparison to AlPcCl are set forth in Table 1 below.

Clonogenic cell survival

Cells were irradiated at a density of approximately $2 \times 10^6$ per 25 cm$^2$ flask. Immediately after irradiation, the cell monolayer was treated with trypsin, and appropriate aliquots were plated in triplicate to give 100 to 200 colonies in each 10-cm Petri dish. Cell survival was determined by the ability of the cells to form colonies containing at least 50 cells. The response of cells treated with 1 $\mu$M AlPcCl and light was compared in each experiment.

TABLE 1

Activities of Several Al and Si Phthalocyanines

| Compound No. | Structure | Concn. ($\mu$M) | Efficacy Relative to 1 $\mu$M (AlPcCl) | | | |
|---|---|---|---|---|---|---|
| | | | Uptake | Growth Delay (12 kJ/m$^2$) | $F_{10}$ (AlPcCl) / $F_{10}$ (Pc) | $CF_{10}$ (AlPcCl) / $CF_{10}$ (Pc) |
| | AlPcCl | 1.0 | 1.0 | 1.0 | 1.0 | 1.0 |
| I. | AlPcOSi(CH$_3$)$_2$(CH$_2$)$_3$N(CH$_3$)$_2$ | 1.0 | 2.3 | 2.1 | 0.94 | 0.51 |
| II. | AlPcOSi(CH$_3$)$_2$(CH$_2$)$_3$N(CH$_3$)$_3$$^+$I$^-$ | 1.0 | 1.8 | 3.4 | 0.99 | 0.72 |
| III. | CH$_3$SiPcOSi(CH$_3$)$_2$(CH$_2$)$_3$N(CH$_3$)$_2$ | 1.0 | 0.07 | 0.05 | ND | ND |
| IV. | HOSiPcOSi(CH$_3$)$_2$(CH$_2$)$_3$N(CH$_3$)$_2$ | 0.5 | 1.3 | >3 | 1.85 | 3.9 |
| | | 1.0 | 1.64 | ND | 4.25 | 3.5 |
| V. | HOSiPcOSi(CH$_3$)$_2$(CH$_2$)$_3$N(CH$_3$)$_3$$^+$I$^-$ | 1.0 | 0.3 | 0 | 0.59 | 3.0 |
| VI. | SiPc(OSi(CH$_3$)$_2$(CH$_2$)$_3$N(CH$_3$)$_3$$^+$I$^-$)$_2$ | 1.0 | 0.1 | 0.05 | ND | ND |

Results

All of the compounds have been examined for the extent of cellular uptake after exposure of V79 cells to 1 $\mu$M or less in complete medium, and the data of Table 1 are presented relative to the uptake from 1 $\mu$M AlpcCl, which Was $0.723 \pm 0.172$ nmole/10$^7$ cells (mean $\pm$ S. D., 25 determinations). Compounds I, II, and IV were taken up into the cells more efficiently than was AlPcCl under these conditions. In particular, when the concentration of compound IV was 1 $\mu$M in the medium, the uptake into the cells was sufficiently high that some of the uptake and phototoxicity studies were repeated at 0.5 $\mu$M. Compounds III, V, and VI were poorly incorporated into V79 cells.

Photodynamic action against V79 cells was assessed both by measurement of growth delay and by assay of the loss of clonogenicity. With both assays, none of the compounds showed any dark toxicity at concentrations of 1.0 $\mu$M or less for up to 18 hours.

The inhibition of V79 culture growth was measured during a three day period following red light irradiation (12 kJ/m$^2$) of phthalocyanine-pretreated cells. With each of the active compounds, as well as with AlPcCl, there was an initial decrease in cell density, as dead cells became detached from the monolayer. Thereafter, the cell number per flask increased, as living cells grew and divided. The time for the cell density to recover to the level at the time of light exposure was considered the growth delay. Cells treated with 1 $\mu$M AlPcCl for 18 hours and 12 kJ/m$^2$ light were used for comparison purposes in each experiment and demonstrated a growth delay of approximately 24 hours. The ratio of the growth delay for the test photosensitizer and the growth delay for AlPcCl measured in the same experiment is recorded in Table 1. There was little or no inhibition of culture growth when cells were exposed to compounds III, V, or VI as expected from the poor cellular uptake of these drugs. In contrast, substantial inhibition was observed for compounds I, II, and IV. A value of >3 for compound IV (Table 1) indicates that the cell density had not recovered to the initial level during the three day observation period.

Photocytotoxicity of the new phthalocyanines was also assessed by clonogenic assay (Table 1, FIG. 1). In all experiments, 1 $\mu$M AlPcCl was included for comparison purposes. From the survival curves (FIG. 1), the fluence reducing the cell survival to 10% (F$_{10}$) was obtained. The ratio of the F$_{10}$ for AlPcCl and the F$_{10}$ for the test compound is recorded in Table 1. Compounds I and II appear to be nearly as efficient photosensitizers as AlPcCl, while compound IV (assayed at half the concentration) was almost twice as efficient as the standard AlPcCl. Clonogenic assays were not conducted for compounds III and VI, since the data on uptake and growth delay suggested that these compounds would have poor activity. However, in spite of the low efficiency of compound V in inhibiting cell growth, survival measurements were made for this compound, because it was taken up into V79 cells somewhat more efficiently than compounds III and VI.

Figure 2:
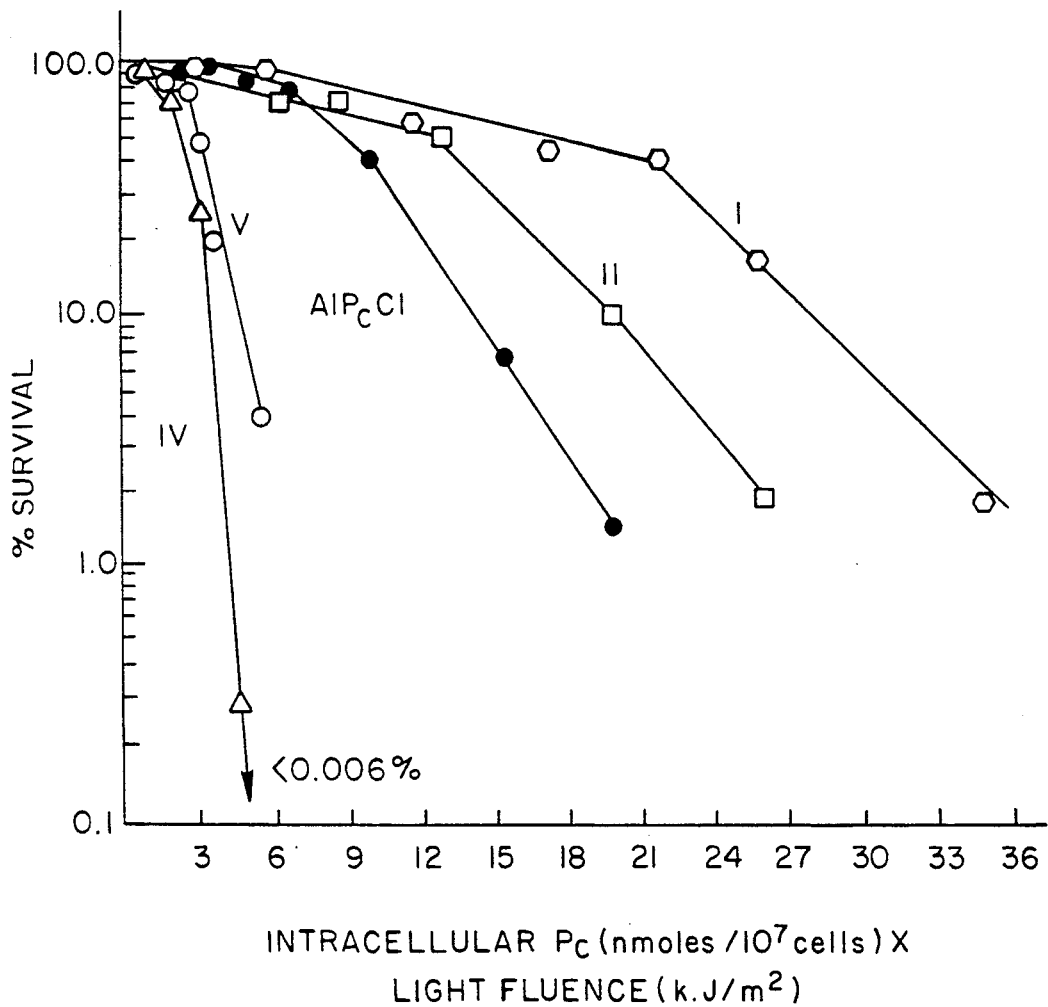
FIG. 2 is a graph demonstrating the percent survival of the compositions of the present invention in comparison to AlPcCl in relation to intracellular phthalocyanine (nmoles/$10^7$ cells) and light fluence (kJ/$m^2$). In this regard, in FIG. 2 the data of FIG. 1 were replotted as a function of the product of the amount of cell-associated phthalocyanine and the light fluence.

In order to take differences in cellular uptake into consideration in the assessment of the relative efficiency of these phthalocyanines as photosensitizers of V79 cells, the survival data were replotted against the product of intracellular phthalocyanine concentration and light fluence (FIG. 2). From these curves, the product of intracellular concentration and light fluence reducing survival to 10% ($CF_{10}$) was obtained, and comparisons of the values for AlPcCl and the test compounds are recorded in Table 1. By this and the other criteria, compound IV appears to be the most efficient photosensitizer. However, when consideration is given to the lesser cell uptake of compound V, it appears to be about as strong a photosensitizer as compound IV.

DISCUSSION

Photocytotoxicity

The low activity of compounds III and VI appears to be due to poor cell uptake. Both of these compounds have functional groups on both faces of the phthalocyanine ring, and it is possible that one face of the ring must be free for proper interaction with target biomolecules. Either Si phthalocyanine with no more than a hydroxyl group on one face (IV) or Al phthalocyanine with one face free of substituents (I and II) allows efficient cellular uptake as well as a high degree of cellular inactivation. Thus, both tertiary and quaternary amines appear to be efficacious structures. Compound V is an anomaly. Although it has features on either face of the phthalocyanine ring found on active molecules, the combination appears not to allow efficient cellular uptake. However, that which is incorporated into the cells has good photodynamic activity.

The results of the in vitro biological tests of the new phthalocyanines are an important introduction to the design of a new class of photosensitizers. The results suggest that tertiary and quaternary amines may be an important class of structures to be explored. The axial ligands of the series of compounds listed in Table 1 are simpler than the corresponding ligand of the original diethylamine which served as a prototype. The simpler ligands appear to have the advantages of stability in solution, making them easier to study. The instability of the diethylamine precluded precise measurements of the concentration of the active species at the time of irradiation. Therefore, the true photosensitizing activity of the prototype compound may also be high.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

In addition, although the present invention has been described with reference to the effectiveness of the phthalocyanine compositions in photodynamic therapy for the destruction of cancer tissue, it is well understood by those skilled in the art that the compositions of the invention may be well suited for other therapeutic purposes. Along this line, it is contemplated that other possible uses of the composition of the present invention include:

(1) the purging of bone marrow for autologous bone marrow transplantation;

(2) the purging of viruses from whole blood or blood components;

(3) the treatment of psoriasis;

(4) the treatment of warts;

(5) the treatment of macular degeneration; and (6) the treatment of intra-arterial plaques.

Thus, the new phthalocyanine compositions of the present invention may be effective for a wide variety of therapeutic uses.

Having thus described the preferred embodiment, the invention is now claimed to be:

1. A phthalocyanine compond of Formula I:

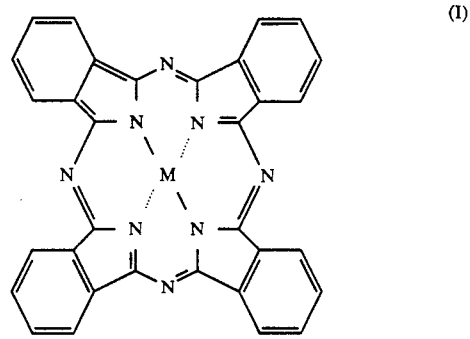

wherein:
M = $AlOSi(CH_3)_2(CH_2)_3N(CH_3)_2$;
$AlOSi(CH_3)_2(CH_2)_3N(CH_3)_3{}^+I^-$;
$HOSiOSi(CH_3)_2(CH_2)_3N(CH_3)_2$; or
$HOSiOSi(CH_3)_2(CH_2)_3N(CH_3)_3{}^+I^-$.

2. A therapeutic composition comprising the phthalocyanine compond according to claim 1 and a pharmaceutical carrier therefor.

3. A synthesized $AlPcOSi(CH_3)_2(CH_2)_3N(CH_3)_2$ produced by a process comprising the steps of:
   a) treating a suspension of $AlPcOH \cdot xH_2O$ and 2-ethylpyridine with $CH_3OSi(CH_3)_2(CH_2)_3N(CH_3)_2$ at an elevated temperature; and,
   b) recovering the product from the reaction mixture by the evaporation of the mixture.

4. A synthesized $AlPcOSi(CH_3)_2(CH_2)_3N(CH_3)_3{}^+I^-$ produced by a process comprising the steps of:
   a) refluxing a mixture of $AlPcOSi(CH_3)_2(CH_2)_3N(CH_3)_2$, benzene and $CH_3I$; and,
   b) recovering the reaction product by the filtration of the reaction mixture.

5. A synthesized $HOSiPcOSi(CH_3)_2(CH_2)_3N(CH_3)_2$ produced by a process comprising the steps of:
   a) irradiating a mixture of $CH_3SiPcOSi(CH_3)_2(CH_2)_3N(CH_3)_2$, $N(C_2H_5)_3$ saturated with $H_2O$, and toluene to produce a suspension; and,
   b) recovering the reaction product by precipitating the reaction product from the reaction mixture with a solvent.

6. HOSiPcOSi(CH$_3$)$_2$(CH$_2$)$_3$N(CH$_3$)$_3$+I$^-$ synthesized by a process comprising the steps of:
   a) refluxing a mixture of HOSiPcOSi(CH$_3$)$_2$(CH$_2$)$_3$N(CH$_3$)$_2$, CH$_3$I and benzene; and,
   b) recovering the reaction product by filtering the reaction mixture.

7. SiPc(OSi(CH$_3$)$_2$(CH$_2$)$_3$N(CH$_3$)$_2$)$_2$ synthesized by a process comprising the steps of:
   a) distilling a mixture of CH$_3$O-Si(CH$_3$)$_2$(CH$_2$)$_3$N(CH$_3$)$_2$ and a suspension of SiPc(OH)$_2$ and 2-ethylpyridine; and,
   b) recovering the reaction product by evaporating the reaction mixture.

* * * * *